(12) United States Patent
Ghosh et al.

(10) Patent No.: US 6,919,465 B2
(45) Date of Patent: Jul. 19, 2005

(54) METHOD OF PREPARING (3R, 3AS, 6AR)-3-HYDROXYHEXAHYDROFURO[2,3,-B]FURAN AND RELATED COMPOUNDS

(75) Inventors: Arun K. Ghosh, River Forest, IL (US); Marcus Noetzel, Burghausen (DE); Sofiya Leshchenko, Wheaton, IL (US)

(73) Assignee: The Board of Trustees of the University of Illinois, Urbana, IL (US)

( * ) Notice: Subject to any disclaimer, the term of this patent is extended or adjusted under 35 U.S.C. 154(b) by 99 days.

(21) Appl. No.: 10/681,637

(22) Filed: Oct. 8, 2003

(65) Prior Publication Data

US 2004/0127727 A1 Jul. 1, 2004

Related U.S. Application Data

(60) Provisional application No. 60/417,379, filed on Oct. 9, 2002.

(51) Int. Cl.[7] .................. C07D 307/28; C07D 493/06
(52) U.S. Cl. ........................ 549/323; 549/464
(58) Field of Search ................. 549/323, 464

(56) References Cited

PUBLICATIONS

A.K. Ghosh et al., *Tetrahedron Letters*, vol. 36, No. 4, pp. 505–508 (1995).
A.K. Ghosh et al., *J. Med. Chem.*, 39, pp. 3278–3290 (1996).

*Primary Examiner*—Taofiq Solola
(74) *Attorney, Agent, or Firm*—Marshall, Gerstein & Borun LLP

(57) ABSTRACT

A method of synthesizing (3R,3aS,6aR)-3-hydroxyhexahydrofuro[2,3-b]furan (I), and related compounds, in high yield and high enantiomeric selectivity is disclosed.

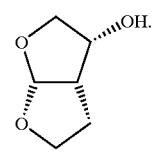

(I)

Also disclosed is a method of manufacturing (5S)-5-(benzyloxymethyl)-5H-furan-2-one.

14 Claims, No Drawings

METHOD OF PREPARING (3R, 3AS, 6AR)-3-HYDROXYHEXAHYDROFURO[2,3,-B]FURAN AND RELATED COMPOUNDS

CROSS REFERENCE TO RELATED APPLICATIONS

This application claims the benefit of U.S. provisional patent application Ser. No. 60/417,379, filed Oct. 9, 2002.

STATEMENT OF GOVERNMENTAL INTEREST

The subject matter of this application has been supported in part by research Grant No. GM53386 from the National Institutes for Health (NIH), Bethesda, Md.

FIELD OF THE INVENTION

The present invention is directed to methods of preparing (3R, 3aS, 6aR)-3-hydroxyhexahydrofuro[2,3-b]furan, having a structural formula (I), stereoisomers of (I), and compounds structurally related to (I).

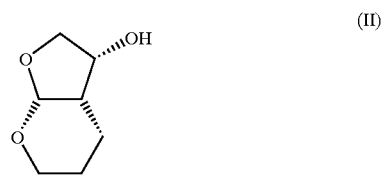

The present invention also is directed to a method of preparing (5S)-5-(benzyloxymethyl)-5H-furan-2-one having a structure

BACKGROUND OF THE INVENTION

Significant advances have been made in the design and synthesis of nonpeptidal ligands for the HIV protease substrate binding site. See, S. Thaisrivong, *Annual Reports on Med. Chem.*, 29, p. 133 (1994). The structure-based design of bis-tetrahydrofuran ligands that can effectively replace two amide bonds and a 10n-aromatic system of an HIV protease inhibitor has been reported (A. K. Ghosh et al., *J. Med. Chem.*, 37, p. 2506 (1994)).

The present commercial method of synthesizing the compound of structural formula (I) provides a racemic mixture, which requires enzymatic resolution to provide optically active ligands with high enantiomeric excess. The preparation of a racemic mixture, and subsequent resolution to provide compound (I), significantly reduces the yield of the desired enantiomer because about one-half of the racemic mixture, i.e., the undesired enantiomer, is wasted. In addition, costs are increased because about one-half of the starting materials and reagents used in the synthesis are wasted.

In particular, the following synthetic scheme (1) illustrates the present commercial method of synthesizing compound (I). This synthesis is disclosed in detail in A. K. Ghosh et al., *Tetrahedron Letters*, 36(4), pp. 505–508 (1995), incorporated herein by reference. Also see, A. K. Ghosh et al., *J. Med. Chem.*, 39, pp. 3278–3290 (1996) for the synthesis of compound (I) and a related compound of structural formula (II) (i.e., (3S,3aR,7aS)-3-hydroxyhexahydrofuro[2,3-b]pyran).

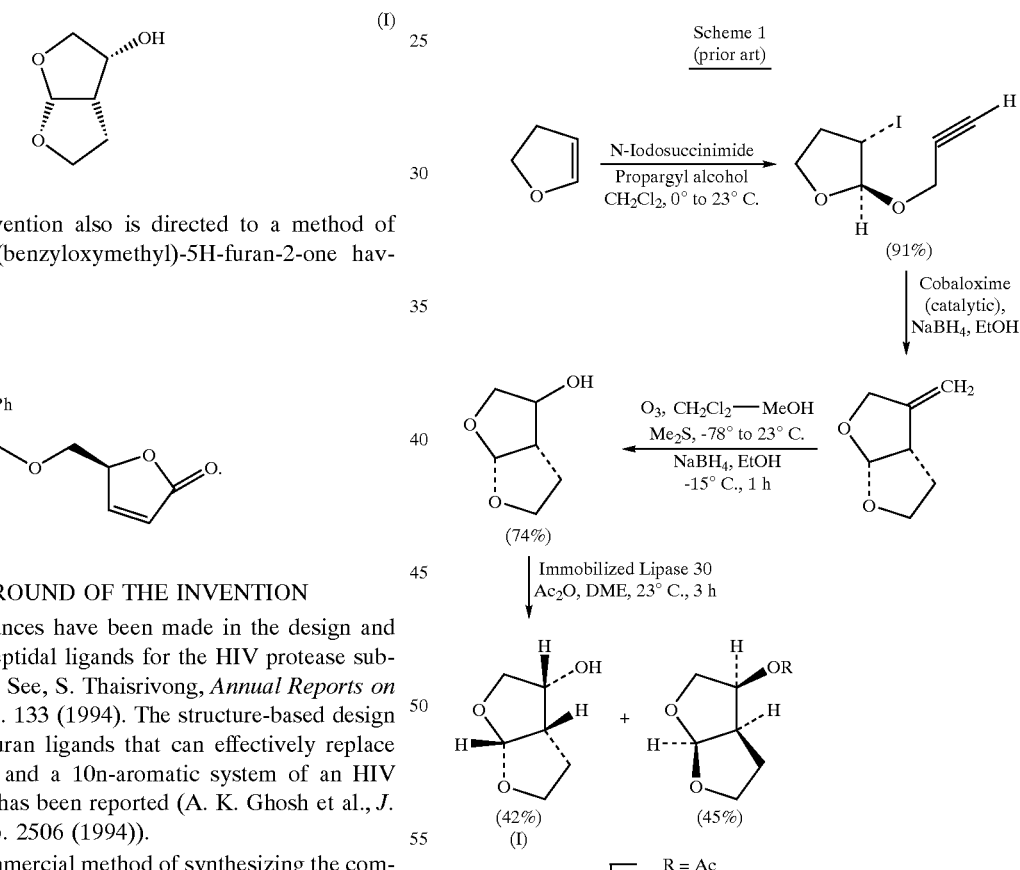

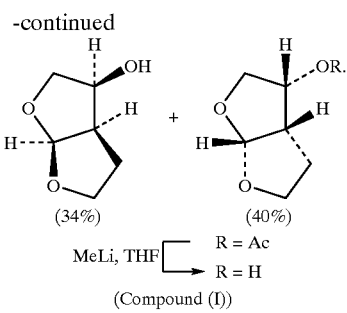

(Compound (I))

There is a need in the art to provide an improved method of synthesizing compound (I), stereoisomers of (I), and related compounds, like compound (II). In particular, a need exists for a short synthetic route that avoids generation of a racemic mixture, and, therefore, increases yield of the desired enantiomer and decreases costs.

There also is a need in the art for an improved synthesis of precursors to compound (I), for example (5S)-5-(benzyloxymethyl)-5H-furan-2-one.

SUMMARY OF THE INVENTION

The present invention relates to methods of preparing (3R,3aS,6aR)-3-hydroxyhexahydrofuro-[2,3-b]furan and related compounds, and to a method of preparing a precursor to compound (I). In particular, the present invention relates to a stereoselective method preparing a compound of structural formula (I), stereoisomers of (I), and related compounds, like the compound of structural formula (II). The present method overcomes disadvantages associated with the present-day commercial synthesis of compound (I), e.g., eliminates the enzymatic resolution of a racemic mixture and increases the yield of the desired enantiomer. The present invention also provides a method of preparing a precursor to compound (I) in high stereoselective yield.

In particular, the present invention is directed to a new and convenient synthesis of (3R,3aS,6aR)-3-hydroxyhexahydrofuro[2,3-b]furan, also termed bis-THF and compound (I), which is an important ligand for several highly potent HIV protease inhibitors, including

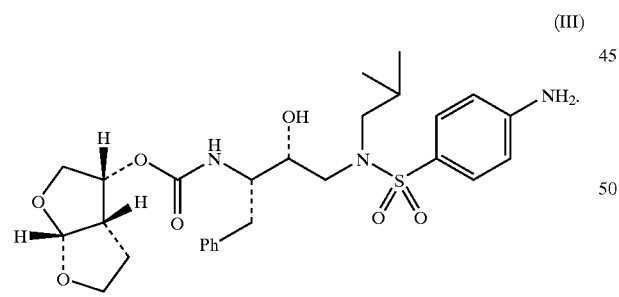

(III)

The method disclosed herein is a new and economical synthesis of an important P$_2$ ligand, i.e., bis-THF, and ligands related in structure to bis-THF. Incorporation of bis-THF in various dipeptide isosteres, including (R)-(hydroxyethyl)aminosulfonamide isosteres, resulted in enhanced potency against wild-type HIV protease, and also against numerous mutant proteases isolated from drug-resistant HIV. The present method also allows (a) synthesis of stereoisomers of bis-THF, (b) incorporation of substituents onto the bis-THF ring system, and (c) variation of ring sizes to optimize HIV protease inhibitor properties, including in vitro potency, in vivo potency, and oral bioavailability.

The present method of synthesizing bis-THF is summarized as follows:

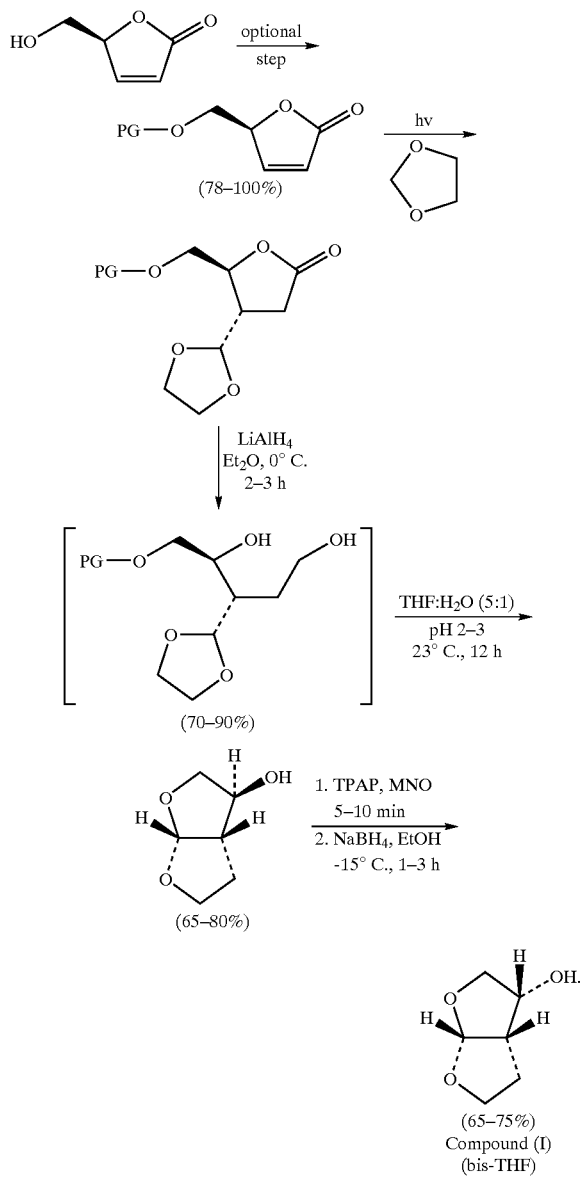

Another aspect of the present invention is to provide a method of preparing a compound having a structure then utilizing the benzyl-protected 5-hydroxymethyl-5H-furan-2-one in the synthesis of compound (I).

Another aspect of the present invention is to provide a method of preparing compounds related to bis-THF by using a starting material having a following structure:

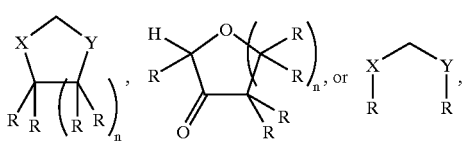

wherein X and Y, independently, are selected from the group consisting of O, S, and NR; each R, independently, is selected from the group consisting of hydro, $C_{1-4}$alkyl, aryl, $C_{1-3}$alkoxy, $C_{1-2}$alkylenearyl; and n is 1, 2, or 3.

Another aspect of the present invention is to provide a method of synthesizing various stereoisomers of bis-THF and compounds related to bis-THF in high stereospecific yield.

In addition, the present invention is directed to methods of preparing protected (5R)-hydroxymethyl-5H-furan-2-ones, such as (5S)-5-(benzyloxymethyl)-5H-furan-2-one.

These and other novel aspects and advantages of the present invention will become apparent from the following detailed description of the preferred embodiments.

DETAILED DESCRIPTION OF THE PREFERRED EMBODIMENTS

The present invention is directed to an efficient, enantioselective synthesis of (3R,3aS,6aR)-3-hydroxyhexahydrofuro[2,3-b]furan (i.e., compound (I) or bis-THF), which is a ligand used in the synthesis of several potent HIV protease inhibitors. For example, compound (III) is currently in clinical trials and contains bis-THF as the $P_2$ ligand. The bis-THF ligand also can be utilized as a component of other therapeutic compounds. The present invention further is directed to methods of synthesizing stereoisomers of bis-THF and synthesizing bicyclic ligands related in structure to bis-THF in high stereospecific yield.

In addition, the present invention is directed to methods of preparing protected (5R)-hydroxymethyl-5H-furan-2-ones, such as (5S)-5-(benzyloxymethyl)-5H-furan-2-one.

The present-day synthesis of bis-THF involves four steps, and yields bis-THF in racemic form. An enzymatic optical resolution of the racemic product provides the desired biologically more active ligand (i.e., bis-THF). The other, less biologically active enantiomer has little value. Thus, the overall synthesis of bis-THF is inefficient. The present synthetic route produces a single, optically pure enantiomer. The present synthetic route also utilizes readily available starting materials, as well as a very efficient, high yield photochemical step.

The present disclosure focuses on the synthetic route to provide bis-THF. However, as disclosed hereafter, substituting a different heterocyclic starting material for 1,3-dioxolane yields compounds related to bis-THF, stereoselectively and in good yield, using the identical synthetic route. The compounds related to bis-THF also can be used as ligands in pharmaceutical compounds, like HIV protease inhibitors. In addition, stereoisomers of bis-THF can be prepared by starting with a different enantiomer of hydroxymethyl-5H-furan-2-one.

The following abbreviations are used in this specification: $CH_2Cl_2$ (methylene chloride), $NaBH_4$ (sodium borohydride), EtOH (ethanol), MeOH (methanol), $Me_2S$ (dimethyl sulfide), h (hour), Ac (acetyl), $Ac_2O$ (acetic anhydride), DME (dimethoxyethane), LiOH (lithium hydroxide), $Et_3N$ (trimethylamine), MeLi (methyl lithium), THF (tetrahydrofuran), PG (protecting group), hv (light), $LiAlH_4$ (lithium aluminum hydride), $Et_2O$ (diethyl ether), $H_2O$ (water), TPAP (tetrapropylammonium perruthenate), MNO (4-methylmorpholine-N-oxide), min (minute), RT (room temperature), MS (molecular sieve), t-Bu (tertiary butyl), $Na_2SO_4$ (sodium sulfate), $CHCl_3$ (chloroform), $CDCl_3$ (deuterated chloroform), $NaHCO_3$ (sodium bicarbonate), Ph (phenyl), g (gram), and $NH_4Cl$ (ammonium chloride).

The synthesis of bis-THF (compound (I)) is summarized below:

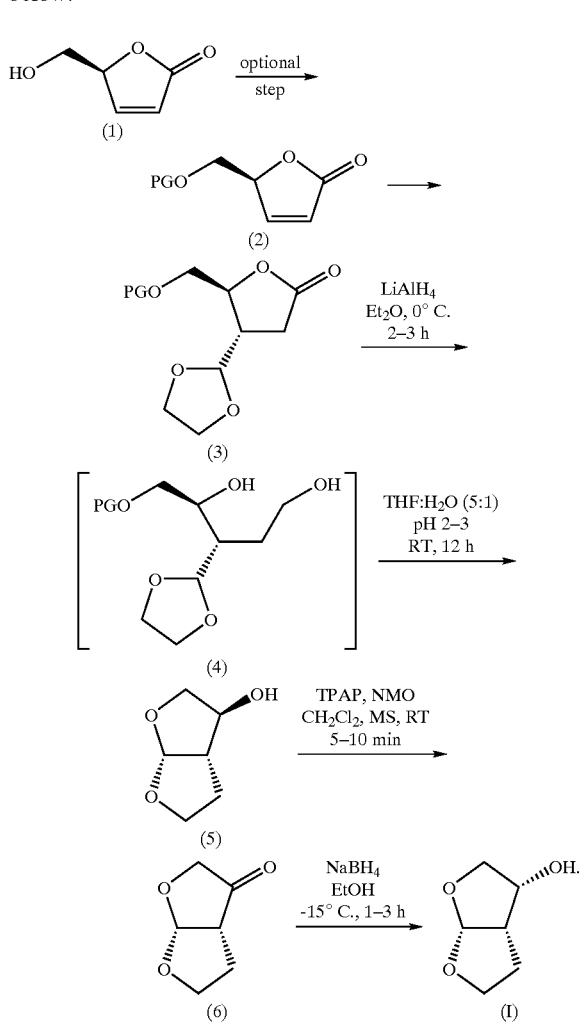

The starting material for the present synthetic route to compound (I) is (5S)-hydroxymethyl-5H-furan-2-one (1). In the first step of the synthesis, the hydroxy group of compound (1) optionally is protected by reacting compound (1) with compound capable of positioning a protecting group (PG) at the hydroxy position of compound (1). This step can be eliminated, and compound (1) can be converted directly to an unprotected compound (3), e.g., PG is H. In some embodiments, use of a PG compound is preferred because subsequent reaction products are easier to isolate.

Protecting group (PG) compounds are utilized in accordance with general principles of synthetic organic chemistry. The identity of the PG compound is not limited and can be any protecting group known to persons skilled in the art. Numerous PG compounds are disclosed in Greene et al., eds., "Protective Groups in Organic Synthesis," Third Edition, John Wiley and Sons, NY, N.Y. (1999) incorporated herein by reference. The protecting groups are removed

5-(tert-Butyldimethylsilanyloxymethyl)-5H-furan-2-one (2a)

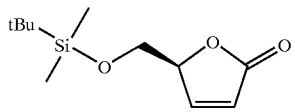

(5S)-5-(tert-Butyldimethylsilanyloxymethyl)-5H-furan-2-one (2a): To a solution containing 199 mg (1.74 mmol) (5S)-hydroxymethyl-5H-furan-2-one (1) and 178 mg (2.61 mmol) imidazole in 10 mL $CH_2Cl_2$, at 0° C., was added 342 mg (2.27 mmol) of tert-butyldimethylsilyl chloride (TBDMS) in one portion. The resulting mixture was stirred for 30 minutes at 0° C. After warming to room temperature, stirring was continued for another 30 minutes. Then 40 mL of water was added, and the organic layer was separated. The aqueous layer was extracted with $CH_2Cl_2$ (3×25 mL), and the combined organic extracts were dried over $Na_2SO_4$. Evaporation of the solvent followed by column chromatography (silica gel 50 g, ethyl acetate in hexanes 20%) yielded compound (2a) (398 mg, 100%) as a colorless solid, $R_f$=0.24, $[\alpha]^{25}_D$ −137°, c 0.9, $CHCl_3$, IR (neat) 2929, 1755, 1256, 837 $cm^{-1}$; $^1$H-NMR (500 MHz, $CDCl_3$) δ: 0.06 (s, 6H), 0.87 (s, 9H), 3.79 (dd, 1H, J=5.5 Hz, J=10.8 Hz), 3.92 (dd, 1H, J=4.5 Hz, J=10.8 Hz), 5.05 ($m_c$, 1H), 6.16 (dd, 1H, J=1.2 Hz, J=4.5 Hz), 7.49 (dd, 1H, J=1.2 Hz, J=5.5 Hz). $^{13}$C-NMR (125.8 MHz, $CDCl_3$, Dept) δ: −5.11 (+), 18.63 (quat), 26.13 (+), 63.33 (−), 83.75 (+), 122.94 (+), 154.75 (+), 173.39 (quat). $C_{11}H_{20}O_3Si$; Exact Mass: 228.12; Mol. Wt.: 228.36; C, 57.85; H, 8.83; O, 21.0; Si, 12.30.

Acetic Acid 5-oxo-2,5-dihydrofuran-2-ylmethyl ester (2c)

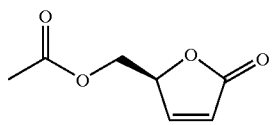

(5S)-5-(Acetyloxymethyl)-5H-furan-2-one (2c): To a solution containing 1.012 g (8.869 mmol) (5S)-hydroxymethyl-5H-furan-2-one (1) in 50 mL of dry pyridine, at 0° C., was added a solution containing 0.631 mL (8.87 mmol) acetyl chloride in 10 mL $CH_2Cl_2$. After stirring for 1 hour at 0° C., the solvent was removed. The residue was dissolved in the $CH_2Cl_2$ (50 mL) and was washed with saturated $NaHCO_3$ solution (50 mL). The organic layer was separated. The aqueous layer was extracted with $CH_2Cl_2$ (3×50 mL), and the combined organic extracts were dried over $Na_2SO_4$. Evaporation of the solvent followed by column chromatography (silica gel 100 g, ethyl acetate in hexanes 50%) yielded compound (2c) (1.27 g, 92%) as a colorless solid, $R_f$=0.31, $[\alpha]^{25}_D$ −134.5°, c 1.3, $CHCl_3$, IR (neat) 1746, 1367, 1218, 767 $cm^{-1}$; $^1$H-NMR (300 MHz, $CDCl_3$) δ: 2.05 (s, 3H), 4.32 (m, 2H), 5.23 (m, 1H), 6.20 (dd, 1H, J=2.2 Hz, J=5.8 Hz), 7.43 (dd, 1H, J=1.6 Hz, J=5.8 Hz). $^{13}$C-NMR (75.4 MHz, $CDCl_3$, Dept) δ: 20.58 (+), 62.55 (−), 80.74 (+), 123.32 (+), 152.32 (+), 170.51 (quat), 172.22 (quat). $C_7H_8O_4$; Exact Mass: 156.04; Mol. Wt.: 156.14; C, 53.85; H, 5.16; O, 40.99.

(5S)-5-Pivaloyloxymethyl)-5H-furan-2-one (2d)

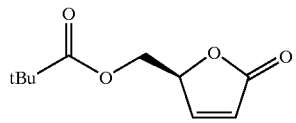

(5S)-5-(Pivaloyloxymethyl)-5H-furan-2-one (2d): To a solution containing 101 mg (0.885 mmol) (5S)-hydroxymethyl-5H-furan-2-one (1) in 10 mL of dry $CH_2Cl_2$ and 79 μL (0.97 mmol) pyridine, at 0° C., was added a solution containing 120 μL (0.973 mmol) pivaloyl chloride in 2 mL $CH_2Cl_2$. After stirring for 3 hours at 0° C., the solution was stirred at room temperature overnight. The solvent then was removed, and the residue was dissolved in $CH_2Cl_2$ (10 mL) and washed with saturated $NaHCO_3$ solution (5 mL). The organic layer was separated, the aqueous layer was extracted with $CH_2Cl_2$ (3×10 mL), and the combined organic extracts dried over $Na_2SO_4$. Evaporation of the solvent followed by column chromatography (silica gel 30 g, ethyl acetate in hexanes 40%) yielded compound (2d) (143 mg, 81%) as a colorless solid, $R_f$=0.20, $[\alpha]^{25}_D$ −138°, c 1.3, $CHCl_3$, IR (neat) 3056, 1756, 1730, 1616, 1172 $cm^{-1}$; $^1$H-NMR (300 MHz, $CDCl_3$) δ: 1.16 (s, 9H), 4.36 (d, 2H, J=4.2 Hz), 5.23 (dd, 1H, J=1.8 Hz, J=4.2 Hz), 6.18 (dd, 1H, J=1.8 Hz, J=5.4 Hz), 7.42 (dd, 1H, J=1.8 Hz, J=5.4 Hz). $^{13}$C-NMR (75.4 MHz, $CDCl_3$, Dept) δ: 26.76 (+), 38.58 (quat), 61.68 (−), 80.78 (+), 122.98 (+), 152.21 (+), 172.03 (quat), 177.76 (quat). $C_{10}H_{14}O_4$; Exact Mass: 198.09; Mol. Wt.: 198.22; C, 60.59; H, 7.12; O, 32.29.

Benzoic acid 5-oxo-2,5-dihydrofuran-2-ylmethyl Ester (2e)

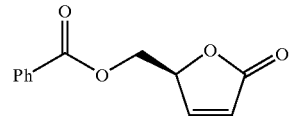

(5S)-5-(Benzoyloxymethyl)-5H-furan-2-one (2e): To a solution containing 94 mg (0.82 mmol) (5S)-hydroxymethyl-5H-furan-2-one (1) in 10 mL of dry pyridine, at 0° C., was added a solution containing 96 μL (0.82 mmol) benzoyl chloride in 1.5 mL $CH_2Cl_2$. After stirring for 1 hour at 0° C., the solvent was removed, and the residue was dissolved in $CH_2Cl_2$ (10 mL) and washed with saturated sodium $NaHCO_3$ (5 mL). The organic layer was separated. The aqueous layer was extracted with $CH_2Cl_2$ (3×10 mL), and the combined organic extracts were dried over $Na_2SO_4$. Evaporation of the solvent followed by column chromatography (silica gel 35 g, ethyl acetate in hexanes 40%) yielded compound (2e) (154 mg, 86%) as a colorless solid, $R_f$=0.30, $[\alpha]^{25}_D$ −119.1°, c 0.8, $CHCl_3$, IR (neat) 1787, 1762, 1772, 1271, 771 $cm^{-1}$; $^1$H-NMR (300 MHz, $CDCl_3$) δ: 4.57 (dd, 2H, J=4.2 Hz, J=9.0 Hz), 5.34 (m, 1H), 6.17 (dd, 1H, J=1.8 Hz, J=5.4 Hz), 7.41 (m, 2H), 7.51

(m, 2H), 7.93 (dd, J=5.1 Hz, J=6.9 Hz). $^{13}$C-NMR (75.4 MHz, CDCl$_3$, Dept) δ: 62.61 (+), 80.71 (−), 123.07 (+), 128.27 (+), 128.81 (quat), 129.37 (+), 133.25 (+), 152.46 (+), 165.69 (quat), 172.10 (quat). C$_{12}$H$_{10}$O$_4$; Exact Mass: 218.06; Mol. Wt.: 218.21; C, 66.05; H, 4.62; O, 29.33

5-(Tetrahydro-pyran-2-yloxymethyl)-5H-furan-2-one (2f)

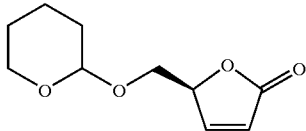

(5S)-5-(Tetrahydropyran-2-yloxymethyl)-5H-furan-2-one (2f): To a solution containing 100.1 mg (0.877 mmol) (5S)-hydroxymethyl-5H-furan-2-one (1) in 10 mL of CH$_2$Cl$_2$ was added, at room temperature, 88 μL (0.97 mmol) dihydropyran and 10 mg (0.053 mmol) p-toluenesulfonic acid. After 8 hours, a saturated NaHCO$_3$ solution (5 mL) was added. The organic layer was separated and the aqueous layer was extracted with CH$_2$Cl$_2$ (3×10 mL). The combined organic extracts were dried over Na$_2$SO$_4$. Evaporation of the solvent followed by column chromatography (silica gel 30 g, ethyl acetate in hexanes 60%) yielded compound (2f) (136 mg, 78%) as a colorless solid, R$_f$=0.23, [α]$^{25}_D$ −129°, c 0.8, CHCl$_3$; $^1$H-NMR (300 MHz, CDCl$_3$) δ: 1.20–1.80 (m, 6H), 3.41–3.51 (m, 1H), 3.58–3.62 (m, 1H), 3.67–3.81 (m, 1H), 3.82–3.95 (m, 1H), 4.56–4.58 (m, 0.5H), 4.60–4.63 (m, 0.5H), 5.15–5.19 (m, 1H), 6.13–6.15 (m, 1H), 7.49–7.51 (m, 1H). C$_{10}$H$_{14}$O$_4$; Exact Mass: 198.09; Mol. Wt.: 198.22; C, 60.59; H, 7.12; O, 32.29.

The following Table 1 summarizes the optional first step of the present synthetic sequence, i.e., protecting the hydroxy group of compound (1) to provide a protected compound (2).

TABLE 1

Preparation of Protected Compounds

| Product | Protecting Group | Yield (%) |
|---|---|---|
| 2a | TBDMS | 100 |
| 2b | TMS[a] | (b) |
| 2c | COCH$_3$ | 100 |
| 2d | COt-Bu | 93 |
| 2e | COPh | 85 |
| 2f | THP | 78 |
| 2g | MOM | 82 |

[a]TMS is trimethylsilanyl.
[b]Complete conversion, product was used crude in next step of the synthetic sequence.

Compound (1) or a protected compound (2) then is subjected to a photochemical reaction with a compound having heteroatoms. In the synthetic route to bis-THF, compound (1) or a protected compound (2) is reacted with 1,3-dioxolane. As discussed hereafter, compounds other than 1,3-dioxolane can be utilized to synthesize bicyclic compounds related to bis-THF.

The general procedure for the photoaddition of 1,3-dioxolane to compound (1) or a hydroxy-protected compound (2) to provide a compound (3) is as follows:

General procedure for the photoaddition of [1,3]-dioxolane to compound (1) or a protected compound (2):

A solution containing compound (1) or a protected compound (2) and benzophenone in [1,3]-dioxolane was degassed for 1 hour in a stream of argon. The reaction flask then was placed in a water-cooled cooling mantel. After the solution was cooled to the desired temperature, the solution was irradiated from a distance of 10 cm using one 450 watt ACE glass medium pressure mercury lamp. After the reaction was completed the solvent was evaporated and the residue purified by column chromatography.

The following examples illustrate the synthesis of a compound (3) from a compound (2).

5-(tert-Butyldimethylsilanyloxymethyl)-4-[1,3]dioxolan-2-yl-dehydro-furan-2-one (3a)

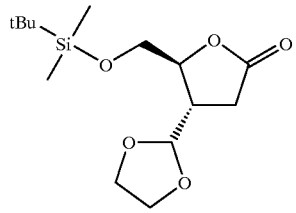

(4S,5S)-5-(tert-Butyldimethylsilanyloxymethyl)-4-[1,3]dioxolan-2-yldihydrofuran-2-one (3a): A solution containing 228 mg (0.998 mmol) compound (2a) and 18.0 mg (0.998 mmol) benzophenone in 200 mL [1,3]-dioxolane was irradiated at 20° C. for 5 hours according to the general procedure. Column chromatography (silica gel 35 g, ethyl acetate in hexanes 30%) gave compound (3a) (285 mg, 94%) as a colorless solid, R$_f$=0.35, [α]$^{25}_D$ 18.3°, c 1.3, CHCl$_3$, IR (neat) 2953, 2857, 1778, 1125 cm$^{-1}$; $^1$H-NMR (300 MHz, CDCl$_3$) δ: 0.05 (s, 6H), 0.87 (s, 9H), 2.45 (dd, 1H, J=4.2 Hz, J=17.7 Hz), 2.68 (d, 1H, J=17.7 Hz), 2.72–2.79 (m, 1H), 3.65 (dd, 1H, J=2.7 Hz, J=11.4 Hz), 3.86–3.91 (m, 3H), 3.97–4.01 (m, 2H), 4.50 (m$_c$, 1H), 4.88 (d, 1H, J=3.6 Hz). $^{13}$C-NMR (75.4 MHz, CDCl$_3$, Dept) δ: 5.52 (+), 18.18 (quat), 25.77 (+), 30.12 (−), 39.67 (+), 64.71 (−), 65.36 (−), 65.47 (−), 80.24 (+), 103.94 (+), 176.55 (quat). C$_{14}$H$_{26}$O$_5$Si; Exact Mass: 302.15; Mol. Wt.: 302.44; C, 55.60, H, 8.67, O, 26.45, Si, 9.29.

(4S,5S)-5-(Acetyloxymethyl)-4-[1,3]dioxolan-2-yldihydrofuran-2-one (3c)

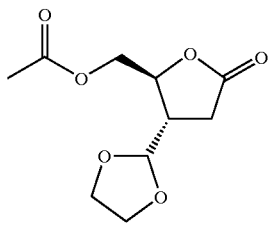

(4S,5S)-5-(Acetyloxymethyl)-4-[1,3]dioxolan-2-yldihydrofuran-2-one (3c): A solution containing 1.20 g (7.69 mmol) of compound (2c) and 107 mg (0.587 mmol) benzophenone in 230 mL [1,3]-dioxolane was irradiated at 0° C. for 8.5 hours according to the general procedure. Column chromatography (silica gel 120 g, ethyl acetate in hexanes 50%) gave compound (3c) (1.63 mg, 92%) as a colorless solid, R$_f$=0.32, [α]$^{25}_D$ 36.2°, c 1.3, CHCl$_3$, IR (neat) 1780, 1745, 1216, 759 cm$^{-1}$; $^1$H-NMR (500 MHz, CDCl$_3$) δ: 2.08 (s, 3H), 2.52 (dd, 1H, J=10.4 Hz, J=21.7 Hz), 2.61–2.66 (m, 2H), 3.84–3.88 (m, 2H), 3.94–3.98 (m, 2H), 4.09 (dd, 1H, J=5.0 Hz, J=12.3 Hz), 4.32 (dd, 1H, J=2.9 Hz, J=12.3 Hz), 4.62 (m$_c$, 1H), 4.87 (d, 1H, J=3.6 Hz). $^{13}$C-NMR (125.8 MHz, CDCl$_3$, Dept) δ: 21.11 (+), 30.16 (−), 40.45 (+), 65.65 (−), 65.78 (−), 65.91 (−), 77.82 (+), 103.54 (+), 170.91 (quat), 175.88 (quat). C$_{10}$H$_{14}$O$_6$; Exact Mass: 230.08; Mol. Wt.: 230.21; C, 52.17; H, 6.13; O, 41.70.

2,2-Dirmethylpropionic acid 3-[1,3]dioxolan-2-yl-5-oxo-tetrahydrofuran-2-ylmethyl Ester (3d)

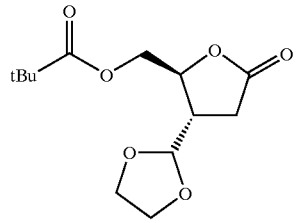

(4S,5S)-5-(Pivaloyloxymethyl)-4-[1,3]dioxolan-2-yldihydrofuran-2-one (3d). A solution containing 29.0 mg (0.146 mmol) compound (2d) and 3.0 mg (0.016 mmol) benzophenone in 20 mL [1,3]-dioxolane was irradiated at 0° C. for 1.5 hours according to the general procedure. Column chromatography (silica gel 15 g, ethyl acetate in hexanes 40%) gave compound (3d) (37 mg. 93%) as a colorless solid, R$_f$=0.21, [α]$^{25}_D$ 23.8°, c 1.0, CHCl$_3$, IR (neat) 1785, 1740, 1210, 740 cm$^{-1}$; $^1$H-NMR (400 MHz, CDCl$_3$) δ: 1.21 (s, 9H), 2.57–2.60 (m, 1H), 2.67–2.75 (m, 2H), 3.91–3.93 (m, 2H), 4.01–4.04 (m, 2H), 4.37 (dd, 1H, J=4.2 Hz, J=12.2 Hz), 4.38 (dd, 1H, J=2.9 Hz, J=12.2 Hz), 4.69 (m$_c$, 1H), 4.92 (d, 1H, J=3.6 Hz). $^{13}$C-NMR (100.6 MHz, CDCl$_3$, Dept) δ: 27.14 (+), 29.75 (−), 38.70 (+) (quat), 65.26 (−), 65.43 (−), 65.58 (−), 77.37 (+), 103.30 (+), 175.47 (quat), 178.02 (quat). C$_{13}$H$_{20}$O$_6$; Exact Mass: 272.13; Mol. Wt.: 272.29; C, 57.34, H, 7.40, O, 35.25.

(4S,5S)-5-(Benzoyloxymethyl)-4-[1,3]-dioxolan-2-yldihydrofuran-2-one (3e)

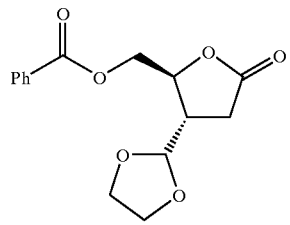

(4S,5S)-5-(Benzoyloxymethyl)-4-[1,3]dioxolan-2-yldihydrofuran-2-one (3e). A solution containing 180 mg (0.825 mmol) compound (2e) and 22.5 mg (0.123 mmol) benzophenone in 110 mL [1,3]-dioxolane was irradiated at 20° C. for 7 hours according to the general procedure. Column chromatography (silica gel 40 g, ethyl acetate in hexanes 40%) gave compound (3e) (193 mg. 80%) as a colorless solid, R$_f$=0.29, [α]$^{25}_D$ 35.2°, c 1.2, CHCl$_3$, IR (neat) 2360, 2342, 1779, 1721, 1272, 1118 cm$^{-1}$; $^1$H-NMR (400 MHz, CDCl$_3$) δ: 2.53 (d, 1H J=11.6 Hz), 2.62–2.73 (m, 2H), 3.83 (m$_c$, 2H), 3.94 (m$_c$, 2H), 4.37 (dd, 1H, J=5.1 Hz, J=12.3 Hz), 4.53 (dd, 1H, J=2.9 Hz, J=12.3 Hz), 4.74 (ddd, 1H, J=2.9 Hz, J=5.1 Hz, J=6.9 Hz), 4.88 (d, 1H, J=3.4 Hz), 7.37 (dd, 2H, J=7.7 Hz, J=7.9 Hz), 7.49 (dd, 1H, J=1.0 Hz, J=7.7 Hz), 7.92 (dd, 2H, J=1.0 Hz, J=7.9 Hz). $^{13}$C-NMR (100.6 MHz, CDCl$_3$, Dept) δ: 29.77 (−), 40.06 (+), 65.37 (−), 65.50 (−), 65.99 (−), 77.56 (+), 103.14 (+), 128.51 (+), 129.31 (quat), 129.57 (+), 133.30 (+), 166.00 (quat) 175.62 (quat). C$_{15}$H$_{16}$O$_6$; Exact Mass: 292.09; Mol. Wt.: 292.28; C, 61.64, H, 5.52, O, 32.84.

4-[1,3]Dioxolan-2-yl-5-(tetrahydropyran-2-yloxymethyl)-dihydrofuran-2-one (3f)

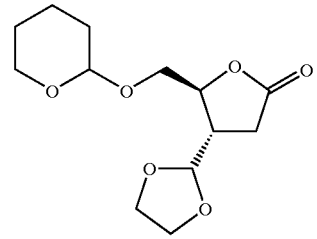

(4S,5S)-4-([1,3]Dioxolan-2-yl)-5-(tetrahydropyran-2-yloxymethyl)-dihydrofuran-2-one (3f): A solution containing 136 mg (0.686 mmol) compound (2f) and 18.7 mg (0.103 mmol) benzophenone in 100 mL [1,3]-dioxolane was irradiated at 20° C. for 5.75 hours according to the general procedure. Column chromatography (silica gel 40 g, ethyl acetate in hexanes 60%) gave compound (3f) as two diastereomers (170 mg, 91%) as a colorless oil, R$_f$=0.25, [α]$^{25}_D$ −129°, c 0.8, CHCl$_3$. $^1$H-NMR (300 MHz, CDCl$_3$) δ: 1.38–1.82 (m, 6H), 2.40–2.46 (m, 1H), 2.60–2.75 (m, 2H), 3.39–3.48 (m, 1H), 3.61–3.70 (m, 1H), 3.75–3.81 (m, 2H), 3.84–3.87 (m, 2H), 3.93–3.98 (m, 2H), 4.53–4.63 (m, 2H), 4.86–4.89 (m, 1H). $^{13}$C-NMR (75.4 MHz, CDCl$_3$, Dept) diastereomer A: δ: 18.72 (−), 25.20 (−), 29.98 (−), 30.02 (−), 40.08 (+), 61.52 (−), 64.68 (−), 65.33 (−), 68.33 (−), 78.98 (+), 98.21 (+), 103.64 (+), 176.51 (quat); B: δ: 19.23 (−), 25.20 (−), 30.21 (−), 30.24 (−), 40.08 (+), 62.20 (−), 65.05 (−), 65.45 (−), 68.81 (−), 79.08 (+), 99.09 (+), 103.71 (+), 176.72 (quat). C$_{13}$H$_{20}$O$_6$; Exact Mass: 272.13; Mol. Wt.: 272.29; C, 57.34; H, 7.40; O, 35.25.

The following Table 2 summarizes the preparation of a compound (3) from a protected compound (2).

| Protecting Group | Yield of (3) (%) | d.r.[d] | % of Ph$_2$CO | Reaction conditions | Yield of a Compound (4) (%)[b] | Yield of a Compound (5) (%) |
|---|---|---|---|---|---|---|
| None (H) | Not isolated | 94:6 | 100 | [1,3]-dioxolane 20° C., 7 h | 89 | 69 |
| TBDMS | 36 | 76:24 | 150 | 20° C., 4.25 h | | |
| TBDMS | 79 | 96:4 | 10 | 20° C., 5 h | | |
| TBDMS | 94 | 97:3 | 10 | 20° C., 5 h | 98 | 81 |
| TBDMS | Pro + dec[a] | — | — | 20° C., 5 h | | |

-continued

| Protecting Group | Yield of (3) (%) | d.r.[d] | % of Ph₂CO | Reaction conditions | Yield of a Compound (4) (%)[b] | Yield of a Compound (5) (%) |
|---|---|---|---|---|---|---|
| TMS | 50 | 96:4 | 8 | 6° C., 3 h | | |
| COCH₃ | Pro + bypr[b] | — | 8 | 20° C., 3.75 h | | |
| COCH₃ | 90 | 94:6 | 9 | 20° C., 1 h | | |
| COCH₃ | | | | 20° C., 1 h, toluene: [1,3]-dioxolane 3:1 | | |
| COCH₃ | 91 | 96:4 | 8 | 6° C., 6 h[c] | 87 | 56 |
| COPh | | | | 20° C., 5.75 h | | |
| THP | 91 | 96:4 | 15 | 20° C., 5.75 h | 95 66 | 68 |
| MOM | — | — | 100 | [1,3]-dioxolane, 20° C., 5 h | | |
| MOM | — | — | 100 | [1,3]-dioxolane, 20° C., 7 h | | |

[a]no further investigation, due to product decomposition or by-product formation.
[b]yield of the crude product; crude product was used directly for cyclization.
[c]large scale, therefore, longer reaction time was necessary.
[d]d.r. is diastereomeric ratio.

In the next step of the present method, a compound (3) is reduced to provide compound (4), followed by a cyclization reaction to provide compound (5) using the following general procedure.

General Procedure for the reduction of a compound (3) followed by cyclization to give (3S,3aS,6aR)-3-hydroxyhexahydrofuro[2,3-b]furan (compound (5)):

To a solution of lithium aluminum hydride in Et₂O or THF was added a solution of a compound (3) in THF, dropwise at 0° C. After 2 hours, the reaction was quenched at 0° C. with an aqueous saturated Na₂SO₄ solution. The solvent was decanted and the remaining precipitate was washed with THF (3×), ethyl acetate (3×), and CHCl₃ (3×). The combined organic extracts were dried over Na₂SO₄. Evaporation of the solvent gave a protected (2S,3S)-3-[1,3] dioxolan-2-ylpentane-1,2,5-triol (compound 4), which was immediately used crude in the next reaction. Compound 4 was dissolved in a mixture THF:water (5:1). At room temperature, the solution was acidified to pH 2–3 with 1N hydrochloric acid. After the reaction was complete, the organic layer was separated. The aqueous layer was extracted with ethyl acetate (3×50 mL), and a solution of 70% CHCl₃, 20% MeOH, and 10% H₂O (3×50 mL). The combined organic extracts were dried over Na₂SO₄, the solvent was evaporated, and the residue was purified by column chromatography.

Hexahydrofuro[2,3-b]furan-3-ol (5)

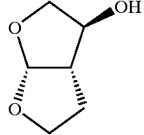

(3S,3aS,6aR)-3-Hydroxyhexahydrofuro[2,3-b]furan (5): According to the above general procedure, a solution containing 216 mg (0.714 mmol) (4S,5S)-5-(tert-butyldimethylsilanyloxymethyl)-4-[1,3]-dioxolan-2-yldihydrofuran-2-one (3a) in THF (25 mL) was reduced with 98 mg (2.58 mmol) LiAlH₄ in THF (7 mL) to give the crude protected triol (4) (132 mg, 96%). The crude triol (4) (76 mg (0.40 mmol)) was cyclized in 6 mL acidified THF:water (5:1). Column chromatography (silica gel 20 g, ethyl methanol in CH₂Cl₂ 10%) gave compound (5) (37.6 mg, 84%) as a colorless solid, R$_f$=0.35, [α]$^{25}_D$ −25°, c 1.0, MeOH. ¹H-NMR (400 MHz, CDCl₃) δ: 1.67 (m$_c$, 1H), 2.14 (m$_c$, 1H), 2.63 (bs, 1H), 2.79 (m$_c$, 1H), 3.75–3.88 (m, 3H), 3.94 (dd, 1H, J=3.0 Hz, J=10.2 Hz), 4.20 (d, 1H, J=2.7 Hz), 5.86 (d, 1H, J=4.9 Hz). ¹³C-NMR (125.8 MHz, CDCl₃, Dept) δ: 29.19 (−), 52.38 (+), 69.52 (−), 75.60 (−), 78.14 (=), 109.23 (+). C₆H₁₀O₃; Exact Mass: 130.06; Mol. Wt.: 130.14; C, 55.37; H, 7.74; O, 36.88.

(3S,3aS,6aR)-3-Hydroxyhexahydrofuro[2,3-b]furan (5): According to the above general procedure, a solution containing 1.44 mg (6.26 mmol) (4S,5S)-5-(acetyloxymethyl)-4-[1,3]dioxolan-2-yldihydrofuran-2-one (3c) in Et₂O:THF 1:1 (20 mL) was reduced with 522 mg (13.75 mmol) LiAlH₄ in Et₂O (100 mL) to give the crude protected triol (4) (1.12 mg, 93%). The crude triol (4) was cyclized in 60 mL THF water (5:1) and 5 mL 1N hydrochloric acid. Column chromatography (silica gel 20 g, ethyl methanol in CHCl₃ 10%) gave compound (5) (515 mg, 64%) as a colorless solid, R$_f$=0.35, [α]$^{25}_D$ −25.1°, c 1.0, MeOH.

Table 2 summarizes the preparation of compounds (4) and (5) from a compound (3).

Tetrahydrofuro[2,3-b]furan-3-one (6)

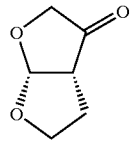

(3aS,6aR)-3-Oxyhexahydrofuro[2,3-b]furan (6): Under a nitrogen atmosphere, a solution containing 440 mg (3.38 mmol) (3S,3aS,6aR)-3-hydroxyhexahydrofuro[2,3-b]furan (5), 599 mg (5.11 mmol) 4-methylmorpholine-N-oxide, and 2 g 4 Å molecular sieves in CH₂Cl₂ (30 mL) was stirred for 20 minutes. Then, tetrapropylammonium perruthenate (36 mg (0.10 mmol)) was added at room temperature. After 5–10 minutes, the reaction mixture was filtered through a pad of silica gel (5 g) with CH₂Cl₂ (100 mL). After evaporation, column chromatography (silica gel 70 g, ethyl acetate in hexanes 40%) gave compound (6) (409 mg. 94%)

as a colorless solid, $R_f$=0.3, $[\alpha]^{25}_D$ −126.6°, c 0.8, CHCl$_3$, IR (Neat) 1758, 1658, 1023 cm$^{-1}$; $^1$H-NMR (400 MHz, CDCl$_3$) δ: 2.23 (m$_c$, 1H), 2.96 (dd, 1H, J=6.8 Hz, J=6.8 Hz), 3.79 (m$_c$, 1H), 3.99 (m, 1H), 4.11 (s, 2H), 6.02 (d, 1H, J=5.0 Hz). $^{13}$C-NMR (100.6 MHz, CDCl$_3$, Dept) δ: 30.38 (−), 49.58 (+), 67.65 (−), 71.69 (−), 107.89 (+), 215.52 (quat). C$_6$H$_8$O$_3$; Exact Mass: 128.05; Mol. Wt.: 128.13; C, 56.24, H, 6.29, O, 37.46.

(3R,3aS,6aR)-3-Hydroxyhexahydrofuro[2,3-b]furan
(I)

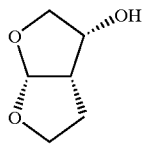

(3R,3aS,6aR)-3-Hydroxyhexahydrofuro[2,3-b]furan (I): To a solution containing 250 mg (1.95 mmol) (3aS,6aR)-3-oxyhexahydrofuro[2,3-b]furan (6) in EtOH (25 mL) was added 89 mg (2.35 mmol) NaBH$_4$ at −18° C. The reaction mixture was stirred at −18° C. for 2.5 hours, then the reaction was quenched with saturated NH$_4$Cl solution (5 mL) and warmed to room temperature. The resulting mixture was concentrated under reduced pressure, and then 10 mL water was added. The aqueous layer was extracted with ethyl acetate (3×50 mL) and a solution of 70% CHCl$_3$, 20% MeOH, and 10% water (3×50 mL). The combined organic extracts were dried over Na$_2$SO$_4$. Column chromatography (silica gel 80 g, MeOH in CHCl$_3$ 7%) gave compound (I) (178 mg. 70%) as a colorless solid, $R_f$=0.3, $[\alpha]^{25}_D$ −12.4°, c 1.3, MeOH. IR (neat) 2951, 1641, 1211 cm$^{-1}$; $^1$H-NMR (400 MHz CDCl$_3$) δ: 1.85 (m$_c$, 1H), 1.94 (bs, 1H), 2.27 (m$_c$, 1H), 2.84 (m$_c$, 1H), 3.63 (dd, 1H, J=7.1 Hz, J=9.2 Hz), 3.89 (m$_c$, 1H), 3.97 (m$_c$, 1H), 4.43 (dd, 1H, J=6.8 Hz, J=14.5 Hz), 5.68 (d, 1H, J=5.2 Hz). $^{13}$C-NMR (125.8 MHz, CDCl$_3$, Dept) δ: 25.27 (−), 46.97 (+), 70.31 (−), 71.26 (−), 73.50 (+), 109.93 (+). C$_6$H$_{10}$O$_3$; Exact Mass: 130.06; Mol. Wt.: 130.14; C, 55.37, H, 7.74, O, 36.88.

The following synthetic scheme illustrates the synthesis of another protected furan-2-one, i.e., compound (13), and an alternative synthesis of bis-THF (I) from compound (5). An important intermediate, i.e., racemic allylic alcohol (8), was prepared in multigram quantities by treatment of commercially available benzyloxyacetaldehyde (7) with vinylmagnesium bromide in THF at 0° C. for 1 hour. Enzymatic acylation of the racemic alcohol (8) with immobilized lipase PS-30 (25% by weight with respect to lipase PS-30) in the presence of isopropenyl acetate in dimethoxyethane (DME) at 23° C. for 23 hours provided the best yield. These conditions provided the optically active desired enantiomer (9) (43% yield, >99% ee) and the acylated alcohol 10 (54% yield), which were separated by silica gel chromatography as set forth in the following synthetic scheme. The optical purity of compound (9) was determined by formation of the Mosher ester and $^{19}$F-NMR analysis (J. A. Dale et al.,*J. Org. Chem.*, 34, 2543 (1969)). A control experiment without the enzyme proved that the nonenzymatic reaction was extremely slow (i.e., only trace amount of acylated product was formed after 48 hours at 23° C.). The acetate (10) can be readily converted to 2-(S)-1-benzyloxy-but-3-en-2-ol (9) using a three-step sequence including: (1) saponification of compound (10) with K$_2$CO$_3$ in MeOH at 23° C. for 35 minutes to provide (R)-1-benzyloxy-but-3-en-2-ol (11); (2) Mitsunobu inversion (S. F. Martin et al., *Tetrahedron Lett.*, 32, 3017 (1991) and O. Mitsunobu, *Synthesis* (1981)) of the resulting 2-(R)-alcohol with Ph$_3$P, p-NO$_2$-benzoic acid in the presence of diisopropylazodicarboxylate (DIAD) at 23° C. for 40 minutes; and (3) aqueous lithium hydroxide promoted saponification of the resulting benzoate derivative. The (S)-alcohol (9) thus obtained (87% overall in 3 steps) has high optical purity (>96% ee) after formation of the Mosher ester and $^{19}$F-NMR analysis. The absolute configurations of the resolved alcohols were assigned based upon comparison of optical rotation with the literature data (A. V. Rao et al., *Tetrahedron Lett.*, 26, 2497–6500 (1987)).

Optically active allylic alcohol (9) was converted to acrylate ester (12) by reaction with acryloyl chloride and Et$_3$N in CH$_2$Cl$_2$ at 0° C. for 10 minutes. Acrylate ester (12) was isolated in 92% yield after silica gel chromatography. Olefin metathesis of (12) with commercially available Grubbs' second generation catalyst (Cl$_2$(PCy$_3$) (IMes)Ru=CHPh, 4 mol %) in refluxing CH$_2$Cl$_2$ for 5 hours, provided the α,β-unsaturated γ-lactone (13) in 98% yield (R. H. Grubbs et al., *Tetrahedron*, 54, 4413 (1998)).

Irradiation of compound (13) in the presence of 1,3-dioxolane and a catalytic amount of benzophenone using 450 watt mercury lamp for 9 hours provided dioxolane derivative (14) in 82% yield. Catalytic hydrogenation of compound (14) over 10% Pd—C in MeOH afforded alcohol (15) in 89% yield. Reduction of compound (15) with lithium aluminum hydride followed by acid catalyzed cyclization furnished bis-tetrahydrofuran derivative (5) in 77% yield in 2-steps. TPAP oxidation of compound (5) provided compound (6) which was reduced with sodium borohydride (NaBH$_4$) to provide optically active bis-tetrahydrofuranyl alcohol (I) as described previously.

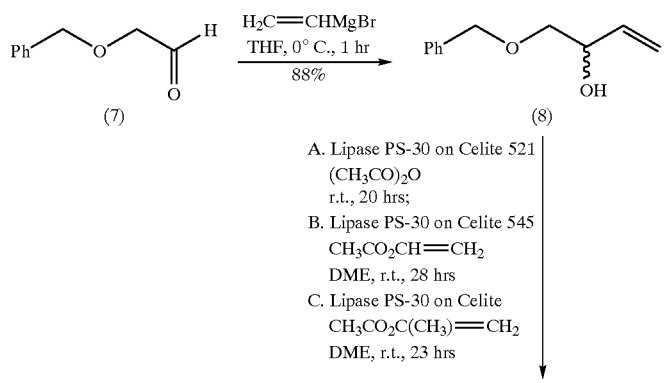

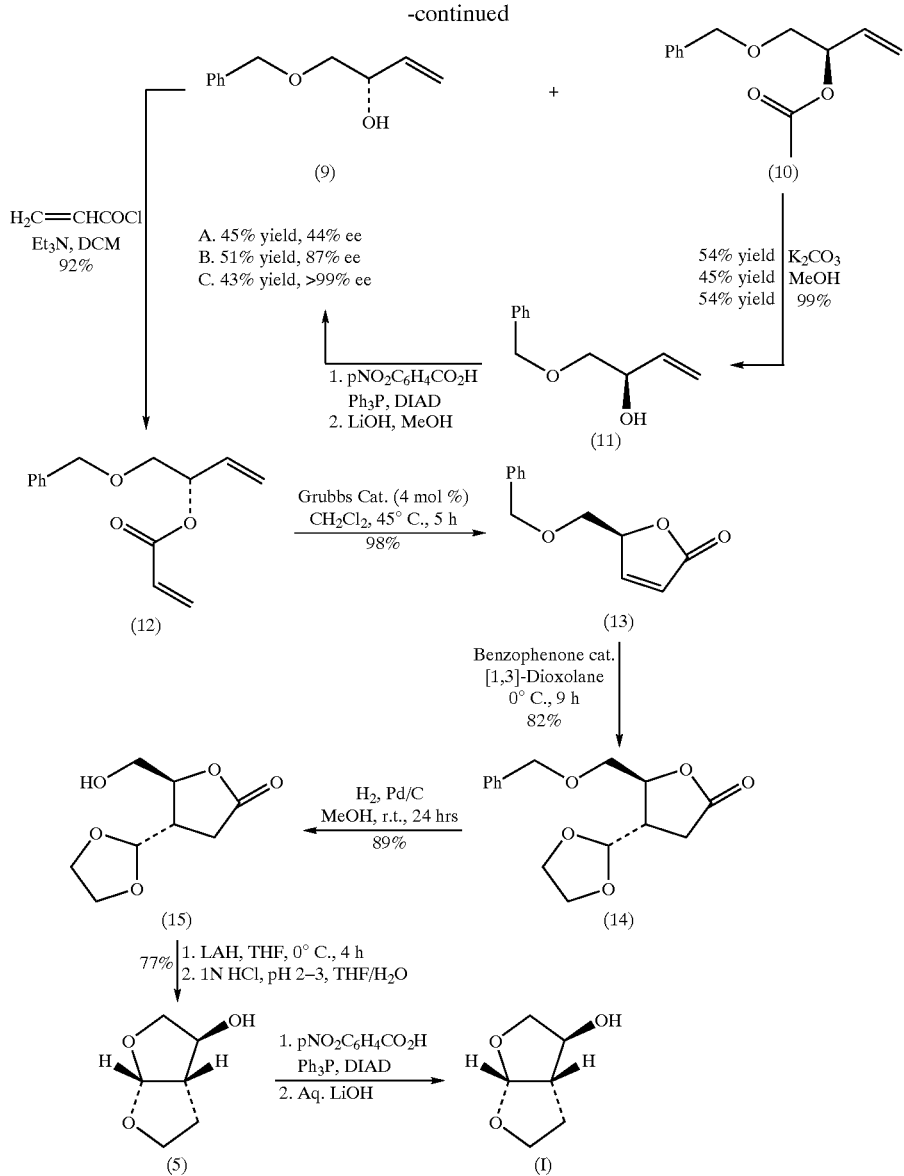

Epimeric alcohol (5) also was converted to desired bis-THF (I) using a two-step sequence involving: (1) Mitsunobu inversion of compound (5) using triphenylphosphine (Ph₃P) and p-nitrobenzoic acid in the presence of diisopropylazodicarboxylate and (2) aqueous lithium hydroxide promoted saponification of the resulting benzoate derivative to provide bis-THF (I).

Experimentals:

1-(Benzyloxy)-but-3-en-2-ol (±)-(8): To a solution of vinylmagnesium bromide (1 M in THF, 40 mL, 40 mmol) in THF (10 mL) at 0° C. was added benzyloxyacetaldehyde (7) (5 g, 33.3 mmol) dropwise. The mixture was stirred for 10 min at 0° C., and the reaction then was quenched with 20 mL of saturated NaHCO₃ solution. The layers were separated, the aqueous layer was extracted with ethyl acetate (3×20 mL), and the combined organic extracts were dried over sodium sulfate. Evaporation of solvent under reduced pressure, followed by column chromatography on silica gel (20% EtOAc in hexanes as the eluent) yielded alcohol (±)-8 (5.22 g, 88%) as a yellow oil, $R_f$=0.40 (30% EtOAc in hexanes); ¹H-NMR (400 MHz, CDCl₃) δ: a 2.79 (bs, 1H), 3.39 (dd, 1H, J=1.7, 7.85 Hz), 3.55 (dd, 1H, J=3.35, 6.3 Hz), 4.35 (m, 1H), 4.58 (s, 1H), 5.21 (dt, 1H, J=7.75, 1.4 Hz), 5.38 (dt, 1H, J=14.18, 1.4 Hz), 5.84 (m, 1H), 7.30–7.38 (m, 5H); ¹³C-NMR (100.6 MHz, CDCl₃) δ: 71.52, 73.37, 74.02, 116.49, 127.85, 128.49, 136.58, 137.81.

(S)-1-(Benzyloxy)-but-3-en-2-ol (9) and (R)-1-(benzyloxy)-but-3-en-2-oyl acetate (10):

A: To a solution of alcohol (±)-(8) (5.21 g, 29.3 mmol) in acetic anhydride (14 mL, 147 mmol) and tert-butyl methyl ether (70 mL, 586 mmol) was added immobilized lipase PS-30 (5.3 g) on Celite 521 (Aldrich). The mixture was stirred at room temperature for 20 h, and then filtered through Celite. Removal of solvent under reduced pressure followed, by column chromatography on silica gel (10 and 15% EtOAc in hexanes as the eluents) yielded acetate (10) (3.81 g, 54%) $R_f$=0.57 (30% EtOAc in hexanes) as a clear oil, $[\alpha]^{25}_D$ −2° (c 1, CHCl₃); NMR (500 MHz, CDCl₃) δ: 2.10 (s, 3H), 3.55–3.59 (m, 2H), 4.56 (q, 2H, J=12.2, 14.0 Hz), 5.24 (d, 1H, J=10.6 Hz), 5.32 (d, 1H, J=17.3 Hz), 5.50 (m, 1H), 5.84 (m, 1H), 7.25–7.36 (m, 5H); ¹³C-NMR (125.8 MHz, CDCl₃) δ: 21.62, 71.67, 73.57, 73.59, 118.39, 128.14, 128.84, 133.77, 138.32, 170.63; alcohol 9 (2.34 g, 45%) as a yellow oil, $R_f$=0.40 (30% EtOAc in hexanes), $[\alpha]^{25}_D$ −8.3° (c 1.06, MeOH).

B: To a solution of alcohol (±)-(8) (3.92 g, 22.0 mmol) in vinyl acetate (46 mL, 499 mmol) and ethylene glycol dimethyl ether (46 mL, 440 mmol) was added immobilized lipase PS-30 (4 g) on Celite-545 (Aldrich). The mixture was stirred at room temperature for 28 h, and then filtered through celite. Removal of solvent under reduced pressure, followed by column chromatography on silica gel (10 and 15% EtOAc in hexanes as the eluents) yielded acetate (10) (2.20 g, 45%) $R_f$=0.57 (30% EtOAc in hexanes) as a clear oil, $[\alpha]^{25}_D$ −2.7° (c 1.35, MeOH); alcohol (9) (2.00 g, 51%) as a yellow oil, $R_f$=0.40 (30% EtOAc in hexanes), $[\alpha]^{25}_D$ −11.4° (c 1.6, MeOH).

C: To a solution of alcohol (±)-(8) (30 mg, 0.168 mmol) in isopropenyl acetate (375 µL, 3.36 mmol) and ethylene glycol dimethyl ether (375 µL, 3.61 mmol) was added immobilized lipase PS-30 (35 mg) on Celite-545 (Aldrich). The mixture was stirred at room temperature for 23 h, and then filtered through celite. Removal of solvent under reduced pressure, followed by column chromatography on silica gel (10) and 15% EtOAc in hexanes as the eluents) yielded acetate 10 (20.3 mg, 54%) as an oil, $R_f$=0.57 (30% EtOAc in hexanes), $[\alpha]^{25}_D$ −1.4° (c 1.02, MeOH); alcohol (9) (13 mg, 43%) as a yellow oil, $R_f$=0.40 (30% EtOAc in hexanes), $[\alpha]^{25}_D$ −13.5° (c 1.3, MeOH).

(R)-1-(Benzyloxy)-but-3-en-2-ol (11): To a solution of acetate (10) (3.7 g, 16.9 mmol) in methanol (20 mL) was added $K_2CO_3$ (7 g, 50.6 mmol). The mixture was stirred at room temperature for 35 min. Methanol then was removed under reduced pressure. The resulting solid residue was dissolved in ethyl acetate, washed with saturated $NH_4Cl$ solution and brine, and dried over sodium sulfate. Removal of ethyl acetate under reduced pressure yielded the crude alcohol (11) (3 g, 100%) as a yellow oil, $R_f$=0.40 (30% EtOAc in hexanes), $[\alpha]^{25}_D$ 8.3° (c 1.06, MeOH).

(S)-1-(Benzyloxy)-but-3-en-2-ol (9) from (11): To a solution of crude alcohol (5) (2 g, 11.2 mmol), triphenylphosphine (5.88 g, 22.4 mmol), and 4-nitrobenzoic acid (2.81 g, 16.8 mmol) in benzene (35 mL) was added at room temperature diisopropyl azodicarboxylate (4.35 mL, 22.4 mmol) dropwise. The mixture was stirred for 40 min, followed by the removal of solvent under reduced pressure. All of the crude ester then was dissolved in a mixture of MeOH:$Et_3$N:$H_2$O (20 ml) in the ratio of 4:3:1 and reacted with LiOH (1.64 g, 39.3 mmol) at room temperature. The mixture was stirred for 2 h, followed by the removal of solvent. Column chromatography on silica gel (15% EtOAc in hexanes as the eluent) yielded alcohol (3) (1.64 g, 82%) as a yellow oil, $R_f$=0.40 (30% EtOAc in hexanes), $[\alpha]^{25}_D$ −7.3° (c 0.82, MeOH).

(S)-1-(Benzyloxy)-but-3-en-2-yl acrylate (12): To a solution of alcohol (3) (1 g, 5.61 mmol) in $CH_2Cl_2$ (20 mL) was added acryloyl chloride (685 µL, 8.41 mmol) dropwise, followed by the addition of $Et_3$N (1.56 mL, 11.2 mmol). The resulting mixture was stirred for 10 min, and the solvent then was removed under reduced pressure. Filtration of the concentrated crude acrylate through a pad of silica gel using 15% EtOAc in hexanes, followed by the removal of solvent, yielded acrylate (12) (1.19 g, 92%) as a colorless oil, $R_f$=0.57 (30% EtOAc in hexanes), $[\alpha]^{25}_D$ −5.7° (c 1.09, $CHCl_3$); $^1$H-NMR (500 MHz, $CDCl_3$) δ: 3.59–3.65 (m, 2H), 4.56 (q, 2H, J=12.2, 14.65 Hz), 5.25 (d, 1H, J=10.6 Hz), 5.33 (d, 1H, J=16.8 Hz), 5.57 (m, 1H), 5.84–5.91 (m, 2H), 6.17 (dd, 1H, J=6.9, 10.4 Hz), 6.44 (dd, 1H, J=1.3, 16.2 Hz), 7.27–7.36 (m, 5H); $^{13}$C-NMR (125.8 MHz, $CDCl_3$) δ: 71.62, 73.58, 73.77, 118.49, 128.05, 128.85, 131.52, 133.62, 138.31, 165.79.

(5S)-5-(Benzyloxymethyl)-5H-furan-2-one (13): To a solution of acrylate (12) (1.87 g, 8.05 mmol) in $CH_2Cl_2$ (700 mL) was added second generation Grubbs' catalyst (4 mol %, 170 mg, 0.322 mmol). The reaction mixture was refluxed for 5 hours, and the solvent then was removed under reduced pressure. Column chromatography on silica gel (30% EtOAc in hexanes as the eluent) yielded the furanone (13) (1.62 g, 98%) as a brown oil, $R_f$=0.15 (30% EtOAc in hexanes), $[\alpha]^{25}_D$ −81.3° (c 1.09, MeOH); $^1$H-NMR (500 MHz, $CDCl_3$) δ: 3.66 (dd, 1H, J=5.0, 5.5 Hz), 3.71 (dd, 1H, J=5.0, 5.2 Hz), 4.57 (s, 2H), 5.17 (m, 1H), 6.16 (dd, 1H, J=1.9, 3.8 Hz), 7.29–7.37 (m, 5H), 7.48 (dd, 1H, J=1.4, 4.3 Hz); $^{13}$C-NMR (125.8 MHz, $CDCl_3$) δ: a 69.86, 74.18, 82.61, 123.03, 128.42, 128.95, 137.69, 154.32, 173.19.

(4S,5S)-5-(Benzyloxymethyl)-4-[1,3]dioxolan-2-yldihydrofuran-2-one (14): A solution of furanone (13) (1.2 g, 5.88 mmols) and benzophenone (108 mg, 0.588 mmols) in [1,3]-dioxolane (108 mg) was degassed for 40 min in a stream of argon. The mixture then was irradiated using one 450 watt ACE glass medium pressure mercury lamp, from a distance of 15 cm, for 9 hours. Progress of this reaction was observed via $^1$H-NMR. As the reaction mixture was degassed, and throughout all of the irradiation time, the reaction flask was held in a water cooled cooling mantel. The temperature of the cooling water was constantly maintained near 0° C. Upon completion of the reaction, solvent was removed under reduced pressure, followed by column chromatography on silica gel (35% EtOAc in hexanes as the eluent), yielding the title compound (1.34 g, 82%) as a clear oil, $R_f$=0.14 (30% EtOAc in hexanes), $[\alpha]^{25}_D$ 16.5° (c 1.2, $CHCl_3$); $^1$H-NMR (500 MHz, $CDCl_3$) δ: 2.50 (dd, 1H, J=3.9, 12.9 Hz), 2.70–2.79 (m, 2H), 3.58 (dd, 1H, J=3.5, 7.2 Hz), 3.75 (dd, 1H, J=2.8, 7.9 Hz), 3.87–3.92 (m, 2H), 3.97–4.00 (m, 2H), 4.51 (d, 1H, J=11.9 Hz), 4.57–4.61 (m, 2H), 4.88 (d, 1H, J=3.6 Hz), 7.26–7.36 (m, 5H); $^{13}$C-NMR (125.8 MHz, $CDCl_3$) δ: 30.39, 40.53, 65.77, 71.74, 73.99, 79.52, 104.14, 128.00, 128.89, 138.07, 176.79.

(4S,5S)-4-[1,3]Dioxolan-2-yl-5-hydroxymethyldihydrofuran-2-one (15): To a solution of dihydrofuranone (14) (0.5 g, 1.79 mmol) in MeOH (30 mL) was added Pd/C (25 mg). The mixture was stirred at room temperature under an $H_2$ balloon for 24 hours, and then filtered over Celite. Removal of solvent under reduced pressure, followed by column chromatography on silica gel (35% EtOAc in hexanes as the eluent) yielded the compound (15) (301 mg, 89%) as a white solid, $R_f$=0.28 (50% EtOAc in hexanes), $[\alpha]^{25}_D$ 22° (c 1.32, $CHCl_3$); $^1$H-NMR (500 MHz, $CDCl_3$) δ: 2.54 (dd, 1H, J=6.0, 11.4 Hz), 2.68–2.81 (m, 2H), 3.66 (dd, 1H, J=3.9–8.5 Hz), 3.88–3.95 (m, 3H), 3.97–4.02 (m, 2H), 4.53 (m, 1H), 4.91 (d, 1H, J=3.9 Hz); $^{13}$C-NMR (125.8 MHz, $CDCl_3$) δ: 30.68, 40.12, 64.36, 65.77, 81.07, 103.94, 176.83.

(3S,3aS,6aR)-3-Hydroxyhexahydrofuro[2,3-b]furan (5): To a solution of lithium aluminum hydride (76 mg, 1.98 mmols) in THF (10 ml) at 0° C. was added dihydrofuranone 15 (275 mg, 1.46 mmol) in THF (30 mL) dropwise. Upon completion of the reduction after 4 hours, the reaction was quenched with a saturated aqueous sodium sulfate solution at 0° C. The solvent then was decanted and the remaining residue was washed with THF (3×), EtOAc (3×), and $CHCl_3$ (3×). The organic extracts were combined and the solvent was removed under reduced pressure, yielding a crude (2S,3S)-3-[1,3]dioxolan-2-ylpentane-1,2,5-triol, which was immediately used in the next reaction.

The crude triol was dissolved in a mixture of THF:$H_2$O (8 ml) in the ratio of a 5:1. This solution then was acidified at room temperature to pH 2–3 with 1 N hydrochloric acid, and was stirred for 40 hours. Removal of solvent with the aid of benzene under reduced pressure, followed by column chromatography purification on silica gel (5% MeOH in $CHCl_3$ as the eluent) yielded the compound (5) (145 mg, 77%) as a white solid, $R_f$=0.40 (15% MeOH in $CHCl_3$), $[\alpha]^{25}_D$ −25.1° (c 1.05, $CHCl_3$); $^1$H-NMR (500 MHz, $CDCl_3$) δ:

1.67 (m, 1H), 2.13 (m, 1H), 2.31 (bs, 1H), 2.79 (m, 1H), 3.80–3.88 (m, 3H), 3.95 (dd, 1H, J=3.2, 7.1 Hz), 4.20 (d, 1H, J=3.1 Hz), 5.86 (d, 1H, J=4.9 Hz).

Preparation of bis-THF derivative (I) (by Mitsunobu inversion of compound (5)): To a stirred solution of alcohol (5) (400 mg, 3.07 mmol), triphenylphosphine (1.6 g, 61.4 mmol), and p-nitrobenzoic acid (770 mg, 4.61 mmol) in dry benzene (30 mL) at 23° C. was added diisoproylazodicarboxylate (DIAD, 1.2 mL, 6.14 mmol) dropwise. After 1.5 hours, the mixture was concentrated in vacuo, and the crude ester was dissolved in a (4:3:1) mixture of MeOH:Et$_3$N:H$_2$O (24 mL), then treated with LiOH (450 mg, 10.7 mmol). The solution was stirred at room temperature for 2 h. The mixture then was concentrated under reduced pressure and the residue was chromatographed over silica gel to provide the bis-THF (I) (326 mg, 82%); [α]$^{25}$D −12.4 (c 1.16, MeOH).

The present method also allows for the preparation of stereoisomers of bis-THF. In particular, by using (5R)-hydroxymethyl-5H-furan-2-one, having a structural formula

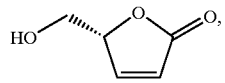

as the starting material in the present yields the following stereoisomers of bis-THF

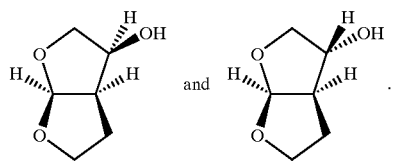

The present method also allows for the preparation of a substituted bis-THF or related bis-THF compound. In particular, the following synthesis illustrates the preparation of a methoxy-substituted derivative (Ia) from compound (1) using methoxymethanol (MOM) as the protecting group in the method of the present invention.

TABLE 3

Preparation of Compound (Ia)

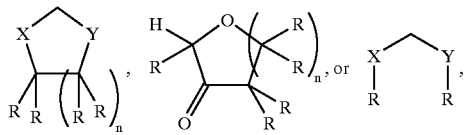

| % of Ph$_2$CO | Reaction conditions |
|---|---|
| — | AIBN, PhH, Δ: |
| 100 | PhH, hv, RT, 7 h |
| 100 | PhH, hv, 23° C., 7 h |

PhH is benzene; AIBN is 2,2'-azobisisobutyronitrile.

In addition, compounds having the same stereochemistry of compound (I), but different substituents, can be synthesized utilizing the method of the present invention. For example, the following compound can be prepared from compound (6) by a reductive amination step.

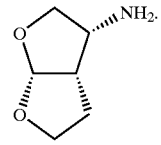

Compound (I) also can be interconverted to a compound related to compound (I). An example of an appropriate interconversion includes, but is not limited to, hydroxy to alkoxy.

The present method also can be used to synthesize bicyclic compounds related to bis-THF. For example, utilizing the same procedure set forth above to synthesize bis-THF, except substituting 1,3-dioxane for 1,3-dioxolane, yields compound (II), stereoselectively, and in good yield. The method also can be used to prepare enantiomers of compound (II) by a proper selection of starting materials and reagents.

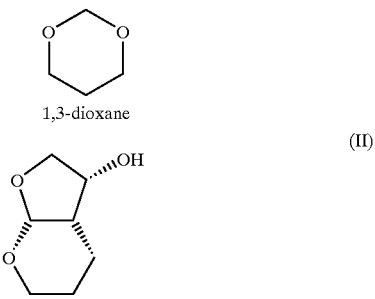

More generally, a cyclic or an acyclic compound having the following general structural formulae can be substituted for 1,3-dioxolane in the present synthetic method:

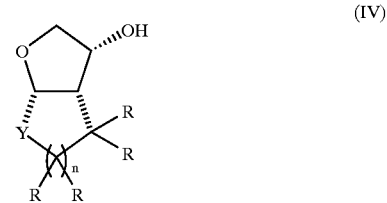

wherein X and Y, independently, are selected from the group consisting of O, S, and NR; each R, independently, is selected from the group consisting of hydro, $C_{1-4}$alkyl, aryl, $C_{1-3}$alkoxy, and $C_{1-2}$alkylenearyl; and n is 1, 2, or 3. Typically, X is O, and Y is O, X, or NR. The R group typically is H, methyl, ethyl, phenyl, benzyl, or OCH$_3$.

Substituting an above-described hetero-atom-containing compound for 1,3-dioxolane provides a compound having a general structural formula (IV).

(IV)

As used herein, the term "$C_{1-4}$alkyl" is defined herein as straight chained and branched hydrocarbon groups containing the indicated number of carbon atoms, i.e., methyl, ethyl, and straight chain and branched propyl and butyl groups.

The term "alkylene" is defined herein as an alkyl group having a substituent. For example, the term "$C_{1-3}$alkylenearyl" refers to an alkyl group containing one to three carbon atoms, and substituted with an aryl group.

The term "aryl" is defined herein as a monocyclic or polycyclic aromatic group, preferably a monocyclic or bicyclic aromatic group, e.g., phenyl or naphthyl. An "aryl" group can be unsubstituted or substituted, for example, with one or more, and in particular one to three, halo, alkyl, alkoxy, alkoxyalkyl, haloalkyl, nitro, and cyano. Exemplary aryl groups include phenyl, naphthyl, tetrahydronaphthyl, chlorophenyl, methylphenyl, methoxyphenyl, trifluoromethylphenyl, nitrophenyl, and the like.

The term "alkoxy" is defined herein as —OR', wherein R' is alkyl.

Modifications and variations of the invention as hereinbefore set forth can be made without departing from the spirit and scope thereof, and, therefore, only such limitations should be imposed as are indicated by the appended claims.

What is claimed is:

1. A method of preparing (3R,3aS,6aR)-3-hydroxyhexahydrofuro[2,3-b]furan comprising:
   (a) optionally reacting (5S)-hydroxymethyl-5H-furan-2-one with a compound capable of positioning a protecting group at the hydroxy position of (5S)-hydroxymethyl-5H-furan-2-one to provide a protected furan-2-one;
   (b) subjecting (5S)-hydroxymethyl-5H-furan-2-one or the protected furan-2-one of optional step (a) to a photochemical reaction in the presence of 1,3-dioxolane to provide a 1,3-dioxolan-substituted furan-2-one;
   (c) reducing the 1,3-dioxolane-substituted furan-2-one of step (b) to provide a reduced product, then hydrolyzing the reduced product to provide a product having a structure

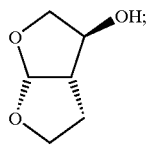

(d) oxidizing the product of step (c) to provide a product having a structure

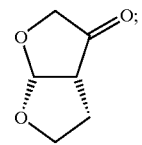

and
   (e) reducing the product of step (d) to provide (3R,3aS,6aR)-3-hydroxyhexahydrofuro[2,3-b]-furan.

2. The method of claim 1 wherein the (3R,3aS,6aR)-3-hydroxyhexahydrofuro[2,3-b]furan is prepared in at least 90% diastereomeric ratio.

3. The method of claim 1 wherein the (3R,3aS,6aR)-3-hydroxyhexahydrofuro[2,3-b]furan is prepared in at least 95% diastereomeric ratio.

4. The method of claim 1 wherein the compound capable of positioning a protecting group at the hydroxy position of (5S)-hydroxymethyl-5H-furan-2-one is selected from the group consisting of an acid chloride, a trialkylsilyl chloride, and a pyran.

5. The method of claim 1 wherein the compound capable of positioning a protecting group at the hydroxy position of (5S)-hydroxymethyl-5H-furan-2-one is selected from the group consisting of tert-butyldimethylsilyl chloride, trimethylsilyl chloride, acetyl chloride, pivaloyl chloride, benzoyl chloride, methoxymethanol, benzyl alcohol, and dihydropyran.

6. A method of preparing (3R,3aS,6aR)-3-hydroxyhexahydrofuro[2,3-b]furan comprising:
   (a) optionally reacting (5S)-hydroxymethyl-5H-furan-2-one with a compound capable of positioning a protecting group at the hydroxy position of (5S)-hydroxymethyl-5H-furan-2-one to provide a protected furan-2-one;
   (b) subjecting (5S)-hydroxymethyl-5H-furan-2-one or the protected furan-2-one of optional step (a) to a photochemical reaction in the presence of 1,3-dioxolane to provide a 1,3-dioxolan-substituted furan-2-one;
   (c) reducing the 1,3-dioxolane-substituted furan-2-one of step (b) to provide a reduced product, then hydrolyzing the reduced product to provide a product having a structure

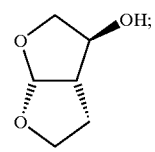

(d) subjecting the product of step (c) to a Mitsunobu inversion utilizing triphenylphosphine, para-nitrobenzoic acid, and diisopropylazodicarboxylate; and
   (e) saponifying the product of step (d) to provide (3R,3aS,6aR)-3-hydroxyhexahydrofuro[2,3-b]furan.

7. A method of preparing a compound having a structure

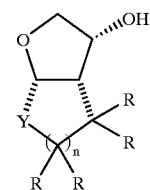

comprising:
   (a) optionally reacting (5S)-hydroxymethyl-5H-furan-2-one with a compound capable of positioning a protecting group at the hydroxy position of (5S)-hydroxymethyl-5H-furan-2-one to provide a protected furan-2-one;
   (b) subjecting (5S)-hydroxymethyl-5H-furan-2-one or the protected furan-2-one of optional step (a) to a photochemical reaction in the presence of a compound having a structural formula

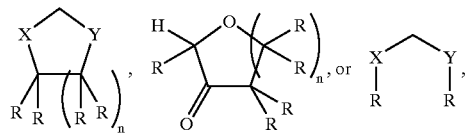

wherein X and Y, independently, are selected from the group consisting of O, S, and NR; each R, independently, is selected from the group consisting of H, $C_{1-4}$alkyl, aryl, $C_{1-3}$alkoxy, and $C_{1-2}$alkylenearyl; and n is 1, 2, or 3, to provide a substituted furan-2-one;

(c) reducing the substituted furan-2-one of step (b) to provide a reduced product, then hydrolyzing the reduced product to provide a product having a structure

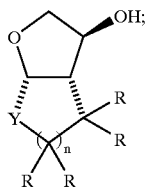

(d) oxidizing the product of step (c) to provide a product having a structure

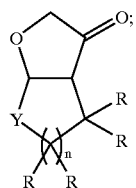

and (e) reducing the product of step (d) to provide the compound having a structure

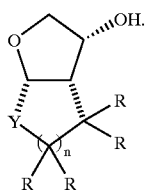

8. A method of preparing a compound having a structure

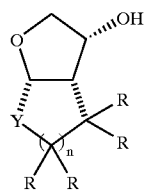

comprising:

(a) optionally reacting (5S)-hydroxymethyl-5H-furan-2-one with a compound capable of positioning a protecting group at the hydroxy position of (5S)-hydroxymethyl-5H-furan-2-one to provide a protected furan-2-one;

(b) subjecting (5S)-hydroxymethyl-5H-furan-2-one or the protected furan-2-one of optional step (a) to a photochemical reaction in the presence of a compound having a structural formula

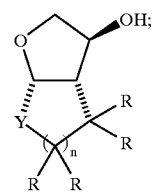

wherein X and Y, independently, are selected from the group consisting of O, S, and NR; each R, independently, is selected from the group consisting of H, $C_{1-4}$alkyl, aryl, $C_{1-3}$alkoxy, and $C_{1-2}$alkylenearyl; and n is 1, 2, or 3, to provide a substituted furan-2-one;

(c) reducing the substituted furan-2-one of step (b) to provide a reduced product, then hydrolyzing the reduced product to provide a product having a structure

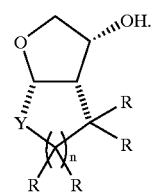

(d) subjecting the product of step (c) to a Mitsunobu inversion utilizing triphenylphosphine, para-nitrobenzoic acid, and diisopropylazodicarboxylate; and (e) saponifying the product of step (d) to provide the compound having a structure 9. A method of preparing

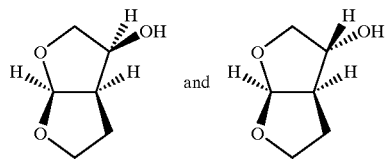

comprising:

(a) optionally reacting (5R)-hydroxymethyl-5H-furan-2-one with a compound capable of positioning a protecting group at the hydroxy position of (5R)-hydroxymethyl-5H-furan-2-one to provide a protected furan-2-one;

(b) subjecting (5R)-hydroxymethyl-5H-furan-2-one or the protected furan-2-one of step (a) to a photochemical reaction in the presence of 1,3-dioxolane to provide a 1,3-dioxolan-substituted furan-2-one; and (c) reducing the 1,3-dioxolan-substituted furan-2-one of step (b) to provide a reduced product, then hydrolyzing the reduced product to provide products having the structures

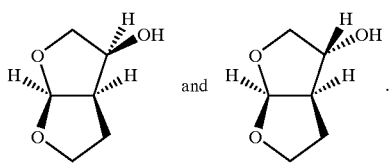

10. A method of preparing a compound having a structure

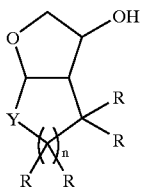

comprising:
(a) optionally reacting a hydroxymethyl-5H-furan-2-one with a compound capable of positioning a protecting group at the hydroxy position of (5S)-hydroxymethyl-5H-furan-2-one to provide a protected furan-2-one;
(b) subjecting the hydroxymethyl-5H-furan-2-one or the protected furan-2-one of step (a) to a photochemical reaction in the presence of a compound having a structure

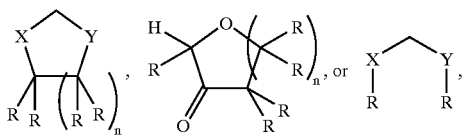

wherein X and Y, independently, are selected from the group consisting of O, S, and NR; each R, independently, is selected from the group consisting of H, $C_{1-4}$alkyl, aryl, $C_{1-3}$alkoxy, and $C_{1-2}$alkylenearyl; and n is 1, 2, or 3, to provide a substituted furan-2-one;
(c) reducing the substituted furan-2-one of step (b) to provide a reduced product, then hydrolyzing the reduced product to provide a product having a structure

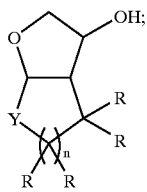

(d) oxidizing the product of step (c) to provide a product having a structure

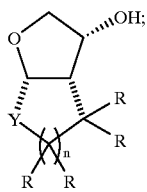

and
(e) reducing the product of step (d) to provide the compound having a structure

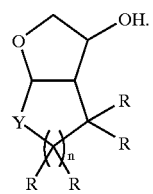

11. A method of claim 10 wherein X and Y are O; each R is H; and n is 1 or 2.

12. A method of preparing a compound having a structure

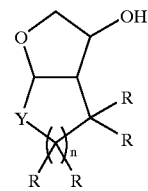

comprising:

(a) optionally reacting a hydroxymethyl-5H-furan-2-one with a compound capable of positioning a protecting group at the hydroxy position of (5S)-hydroxymethyl-5H-furan-2-one to provide a protected furan-2-one;
(b) subjecting the hydroxymethyl-5H-furan-2-one or the protected furan-2-one of step (a) to a photochemical reaction in the presence of a compound having a structure

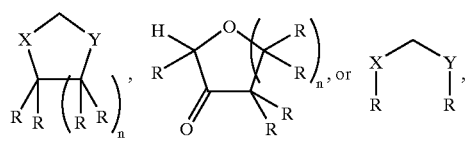

wherein X and Y, independently, are selected from the group consisting of O, S, and NR; each R, independently, is selected from the group consisting of H, $C_{1-4}$alkyl, aryl, $C_{1-3}$alkoxy, and $C_{1-2}$alkylenearyl; and n is 1, 2, or 3, to provide a substituted furan-2-one;
(c) reducing the substituted furan-2-one of step (b) to provide a reduced product, then hydrolyzing the reduced product to provide a product having a structure

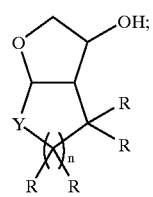

(d) subjecting the product of step (c) to a Mitsunobu inversion utilizing triphenylphosphine, para-nitrobenzoic acid, and dissopropylazodicarboxylate; and (e) saponifying the product of step (d) to provide the compound having a structure

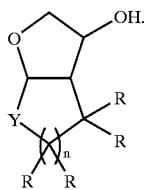

13. A method of preparing a compound having a structure

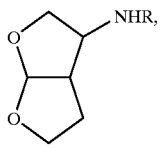

wherein R is selected from the group consisting of H, $C_{1-4}$alkyl, aryl, $C_{1-3}$alkoxy, and $C_{1-2}$alkylenearyl, comprising subjecting a compound having a structure

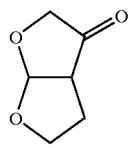

to a reductive amination using an amine having a structure $RNH_2$.

14. A method of preparing (5S)-5-benzyloxymethyl-5H-furan-2-one having a structure

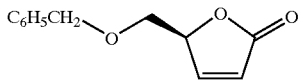

comprising the steps of (a) subjecting (±)-1-(benzyloxy)-but-3-en-2-ol to an enzymatic acylation using immobilized lipase PS-30 and isopropenyl acetate to provide (S)-1-(benzyloxy)-but-3-en-2-ol;

(b) reacting the product of step (a) with acryoyl chloride to provide (S)-1-(benzyloxy)-but-3-en-2-yl acrylate; and (c) interacting the product of step (b) with Grubbs catalyst $(Cl_2PC_3)(IMes)Ru=CHC_6H_5$ to provide (5S)-5-(benzyloxymethyl)-5H-furan-2-one.

* * * * *

UNITED STATES PATENT AND TRADEMARK OFFICE
CERTIFICATE OF CORRECTION

PATENT NO. : 6,919,465 B2
DATED : July 19, 2005
INVENTOR(S) : Ghosh et al.

It is certified that error appears in the above-identified patent and that said Letters Patent is hereby corrected as shown below:

Title page,
Item [54], Title, "METHOD OF PREPARING (3R, 3AS, 6AR) -3-HYDROXYHEXAHYDROFURO [2, 3-B] FURAN AND RELATED COMPOUNDS" should be -- METHOD OF PREPARING (3R, 3aS, 6aR) -3-HYDROXYHEXAHYDROFURO [2, 3-b] FURAN AND RELATED COMPOUNDS --.

Column 28,
Line 66, "dissopropylazodicarboxylate" should be -- diisopropylazodicarboxylate --.

Column 30,
Line 27, "$PC_3$" should be -- ( $PCy_3$ --.

Signed and Sealed this

First Day of November, 2005

JON W. DUDAS
*Director of the United States Patent and Trademark Office*

UNITED STATES PATENT AND TRADEMARK OFFICE
CERTIFICATE OF CORRECTION

PATENT NO. : 6,919,465 B2 Page 1 of 1
DATED : July 19, 2005
INVENTOR(S) : Ghosh et al.

It is certified that error appears in the above-identified patent and that said Letters Patent is hereby corrected as shown below:

Column 1,
Line 13, insert -- The Government has certain rights in this invention. --.

Signed and Sealed this

Seventh Day of March, 2006

JON W. DUDAS
*Director of the United States Patent and Trademark Office*